US009815609B2

(12) United States Patent
Wochele (10) Patent No.: US 9,815,609 B2
(45) Date of Patent: Nov. 14, 2017

(54) DISPENSER FOR LIQUIDS (71) Applicant: APTAR RADOLFZELL GMBH, Radolfzell (DE)

(72) Inventor: Matthias Wochele, Rielasingen-Worblingen (DE)

(73) Assignee: APTAR RADOLFZELL GMBH, Randolfzell (DE)

( * ) Notice: Subject to any disclaimer, the term of this patent is extended or adjusted under 35 U.S.C. 154(b) by 0 days.

(21) Appl. No.: 14/899,322

(22) PCT Filed: May 8, 2014

(86) PCT No.: PCT/EP2014/059498
§ 371 (c)(1),
(2) Date: Dec. 17, 2015

(87) PCT Pub. No.: WO2014/202278
PCT Pub. Date: Dec. 24, 2014

(65) Prior Publication Data
US 2016/0137390 A1    May 19, 2016

(30) Foreign Application Priority Data
Jun. 18, 2013    (DE) .................. 10 2013 211 423

(51) Int. Cl.
*B65D 83/00* (2006.01)
*A45D 34/00* (2006.01)
(Continued)

(52) U.S. Cl.
CPC ......... *B65D 83/0055* (2013.01); *A45D 34/00* (2013.01); *A61J 1/14* (2013.01);
(Continued)

(58) Field of Classification Search
CPC ................ B65D 83/0055; B65D 47/18; B65D 2205/025; A61F 9/0008; A61J 1/14; A45D 34/00
See application file for complete search history.

(56) References Cited

U.S. PATENT DOCUMENTS

| 4,020,978 A | * | 5/1977 | Szczepanski | ......... | B05B 11/046 |
| | | | | | 222/209 |
| 4,842,165 A | * | 6/1989 | Van Coney | ........ | B65D 83/0055 |
| | | | | | 222/105 |

(Continued)

FOREIGN PATENT DOCUMENTS

| DE | 102 16 400 A1 | 10/2003 |
| EP | 1 985 543 A2 | 10/2008 |

(Continued)

OTHER PUBLICATIONS

International Search Report issued in Application No. PCT/EP2014/059498 with English translation, dated Aug. 6, 2014 (6 pages).

(Continued)

Primary Examiner — Frederick C Nicolas
(74) Attorney, Agent, or Firm — Flynn, Thiel, Boutell & Tanis, P.C.

(57) ABSTRACT

A dispenser for discharging a pharmaceutical or cosmetic medium having a discharge head with a discharge opening, a container for storing the medium prior to discharge, an elastically deformable outer container, and a dimensionally flexible inner container arranged in an interior of the outer container. A ventilation channel is provided, through which the interior of the outer container is connected to an environment for pressure compensation by compensating air. The ventilation channel is delimited in at least some regions by a self-adhesive label, or the ventilation channel has a self-adhesive label and has a gas-permeable surface portion. The gas-permeable surface portion is arranged in the ven- (Continued)

tilation channel or on one of the ends of the ventilation channel, such that the air passing through the ventilation channel also passes through the gas-permeable surface portion.

16 Claims, 4 Drawing Sheets

(51) Int. Cl.
    *A61J 1/14*     (2006.01)
    *B65D 47/18*     (2006.01)
    *A61F 9/00*     (2006.01)

(52) U.S. Cl.
    CPC ............ *B65D 47/18* (2013.01); *A61F 9/0008* (2013.01); *B65D 2205/025* (2013.01)

(56) References Cited

U.S. PATENT DOCUMENTS

| | | | |
|---|---|---|---|
| 5,012,956 A * | 5/1991 | Stoody | B65D 83/0055 222/206 |
| 5,275,311 A * | 1/1994 | Piarrat | B65D 35/14 222/105 |
| 5,344,045 A | 9/1994 | Richter et al. | |
| 5,373,967 A | 12/1994 | Grooms et al. | |
| 5,454,486 A * | 10/1995 | Mack | B05B 11/047 222/105 |
| 7,641,078 B2 * | 1/2010 | Boumnso | B65D 83/0055 222/105 |
| 8,118,183 B2 * | 2/2012 | Iwahashi | A61F 9/0008 215/12.2 |
| 2005/0274687 A1 | 12/2005 | McCutchan | |
| 2009/0289073 A1 | 11/2009 | Moore et al. | |
| 2010/0075001 A1 | 3/2010 | Succar et al. | |
| 2010/0147726 A1 | 6/2010 | Timmann et al. | |
| 2014/0144938 A1 | 5/2014 | Kakuta et al. | |

FOREIGN PATENT DOCUMENTS

| | | |
|---|---|---|
| FR | 2 389 419 A1 | 12/1978 |
| WO | WO 2012/169489 A1 | 12/2012 |

OTHER PUBLICATIONS

Office Action of German Patent Office issued in Application No. 10 2013 211 423.0, dated Feb. 19, 2014 (6 pages).

\* cited by examiner

DISPENSER FOR LIQUIDS

FIELD OF USE AND PRIOR ART

The invention relates to a dispenser for discharging a free-flowing pharmaceutical or cosmetic medium, with a discharge head having a discharge opening, and with a container for storing the free-flowing medium prior to discharge. The container has an outer container, and an inner container arranged in the interior of the latter. The outer container is elastically deformable, which is to be understood as meaning that a user can press it together in the manner of a squeeze bottle, in order to reduce its internal volume and thereby discharge liquid, and that the outer container returns to its starting shape after the force ceases to be applied. The inner container arranged in the outer container is the container part that directly receives the medium. Between this inner container and the outer container, a free space is provided which becomes smaller as the inner container is increasingly emptied, since the external volume of the inner container falls as medium is removed, whereas the internal volume of the outer container remains constant.

In order to avoid an underpressure arising in this free space and causing problems in the operation of the dispenser, a ventilation channel is provided in dispensers of the type in question and connects the interior of the outer container to a surrounding atmosphere for the purpose of pressure compensation by means of compensating air.

After a discharge has taken place, said ventilation channel allows air from the environment to be sucked into said free space, such that it is more or less the atmospheric pressure that then once again prevails in the container. However, the ventilation channel is also problematic in principle since, with the outer container being pressed together as intended for the purpose of building up pressure on the inner container and thus for the purpose of discharge, it counteracts the pressure build-up. The slower the actuation by pressing together the outer container, the more air can escape outward through the ventilation channel and thus reduce the amount of the medium that is to be discharged, since the pressure in the free space is not built up to the desired level.

In EP 1 985 543 A2, which relates to subject matter of the generic type, this problem is counteracted by the ventilation channel being intended to be closed by the user, by means of one of his or her fingers, during the actuation. However, this makes handling more difficult.

Problem and Solution

The problem addressed by the invention is that of making available a technical solution by means of which it is possible in a simple way to create a ventilation channel whose flow resistance is dimensioned such that, when the outer container is pressed together, a pressure necessary to discharge the medium can be built up in the inner container.

According to the invention, this problem is solved by the use of a label on the dispenser, which label influences the flow resistance in the ventilation channel in the sense of increasing it.

According to a first aspect of the invention, this ventilation channel, which is also to be understood as meaning a simple ventilation opening, is delimited in at least some regions by said label, which in particular is preferably designed as a self-adhesive label. As has already been mentioned, the label provides the ventilation channel with a flow resistance which is sufficiently high to allow the pressure necessary for the discharge to build up in the inner container.

The at least regional delimitation of the ventilation channel by an in particular self-adhesive label is to be understood as meaning that the label is applied such that, by its application, it increases the flow resistance, wherein, according to this first aspect of the invention, a free path for the air remains macroscopically unclosed by the label. Various types of application for this purpose are explained in more detail below. Generally speaking, it is considered advantageous if the label is applied to the outside of an outwardly accessible surface of the dispenser, in particular on said outer container.

The use of a label is particularly advantageous since it allows the flow resistance to be influenced in a simple way and, through the choice of label and the site of its application, it is possible to influence the characteristics of the ventilation channel according to the specific purpose of its use. Moreover, it is advantageous if the label serves not only to influence the flow resistance but at the same time also constitutes an inscribable label that carries user information, in particular the name of the manufacturer of the dispenser or of the cosmetic or pharmaceutical, directions for use, composition of the content of the dispenser, and so on.

The label used in said context is a thin, film-like surface portion with a thickness of less than 300 μm, preferably of less than 200 μm. This label is applied to a surface and acts there to influence the flow resistance of the ventilation channel. It is preferably a self-adhesive label. Embodiments are also conceivable in principle in which the adhesive for applying the label is applied separately to said surface prior to the application of the label, but a self-adhesive embodiment is of advantage. In individual cases, other methods for applying the label may also be advantageous, for example circumferential shrink-fit labels, or labels that are welded on or secured thermally in some other way.

The outer container can, for example, have the form of a bottle or a tube. It is in particular connected releasably to a discharge head on which the discharge opening is provided. The latter is preferably closed, prior to actuation of the dispenser, by a valve that opens depending on pressure.

In a first type of the configuration in which the flow resistance in the ventilation channel is influenced by the label, provision is made that a channel portion of the ventilation channel penetrates a channel component, wherein this channel component is preferably the outer container. The label is provided with a through-opening, of which the cross-sectional surface area is smaller than the minimal cross-sectional surface area of said channel portion, wherein this through-opening in the label thus also forms a subsidiary portion of the ventilation channel and preferably surrounds the latter circumferentially.

In this configuration, provision is thus made that a subsidiary portion of the ventilation channel, which is greater in terms of its minimal cross section, is provided in particular in the outer container, and the label decreases the minimal cross section of the ventilation channel. It would thus be possible, for example, to provide an opening of 2 mm² in the outer container, which opening is very easy to produce in terms of technology and is reduced to 0.4 mm² by the preferably self-adhesive label. It is in this way very easy to produce small maximum channel cross sections. By the choice of the label and of the through-opening provided therein, it is also possible to permit adaptation to the specific purpose of use.

In an alternative embodiment, provision is made that a channel portion of the ventilation channel is formed jointly by a groove-like elongate depression in a channel component, wherein the channel component is once again preferably the outer container, and that the label is applied to the channel component, such that the channel portion is closed circumferentially by the depression and the adhesive label.

In this variant, provision is thus made that a groove, which can be provided in particular in an outer face of the outer container, is supplemented by the applied label to form a circumferentially closed channel. The flow resistance of the ventilation channel can thus be very easily increased. If a particularly high flow resistance is desired, the cross section of the depression is chosen to be very small. Alternatively or in addition, a particularly long depression can also be used which, for example, can also be easily obtained by a spiral-shaped or helical configuration of the ventilation channel. The environment-side inlet of the ventilation channel is formed by the end of the channel portion which is generated jointly by the depression and the label.

As was already mentioned at the outset, the ventilation channel or the ventilation opening is configured in particular so that the associated flow resistance is such that, when the outer container is pressed together, a pressure sufficient to discharge the medium builds up on the inner container. This is preferably achieved by the fact that the ventilation channel has a flow resistance which is sufficiently high that the volumetric flow rate does not exceed 0.2 ml/s at a pressure difference of 700 mbar between the outer container and the environment. It was found that such a flow resistance, which at an absolute internal pressure of approximately 1.7 bar in relation to an atmospheric pressure of approximately 1 bar allows only 0.2 ml/s to flow out from the space between inner container and outer container, does not negatively influence customary actuations. As an approximation, and not taking account of the change in the influencing factors, an overpressure in the free space between inner container and outer container in relation to the surrounding atmosphere of 0.7 bar thus leads to a maximum air loss of 1 ml from the free space between inner container and outer container at an actuation time of 5 seconds.

However, too high a flow resistance is also undesirable, since this would increase too greatly the length of time needed for the pressure compensation. To be able to use the dispenser again quickly at customary intervals, in particular after 15 to 30 seconds, for example for discharging several batches in a drop dispenser, it is advantageous if the volumetric flow rate is 0.2 ml/s at a pressure difference of 200 mbar.

Overall, therefore, a configuration of the ventilation channel is advantageous which permits a volumetric flow rate of 0.2 ml/s at a pressure difference of between 200 mbar and 700 mbar. It should be noted, however, that the flow resistance for the inward flow of air into the free space and for the outward flow of air out of the free space does not have to be identical, depending on the geometry of the ventilation channel. Generally speaking, the flow resistance of the ventilation channel is configured such that, with outward flow of air at 0.2 ml/sec, an overpressure of 700 mbar must be present, and/or that, for inward flow of air at 0.2 ml/sec, an underpressure of 200 mbar must be present.

It is particularly advantageous, in particular for achieving the preferred flow resistance outlined above, if the ventilation channel is designed in at least some regions as a capillary channel. The latter preferably has a minimal cross-sectional surface area that is smaller than 1 mm². It is particularly advantageous if the quotient of the length of the capillary channel and of the mean cross-sectional surface area of the capillary channel is greater than 150 mm$^{-1}$, in particular greater than 200 mm$^{-1}$, in the region in which the cross-sectional surface area is smaller than 1 mm².

The use of a label, in particular a self-adhesive label, can take place in the manner described above, so that the label influences the flow resistance of the ventilation channel in such a way that the length of the latter is influenced or its minimal cross-sectional surface area is influenced.

In an alternative to this, the dispenser of the type in question according to a second aspect of the invention is designed such that the ventilation channel has a label which is preferably self-adhesive in at least some regions and which has a gas-permeable surface portion, wherein the gas-permeable surface portion is arranged in the ventilation channel or at one of the ends of the ventilation channel in such a way that the air passing through the ventilation channel also passes through the gas-permeable surface portion.

According to this variant, provision is accordingly made that the ventilation channel does not permit a macroscopically completely free path for the compensating air. Instead, a label is provided which is applied in particular at the end of the ventilation channel directed toward the environment and which macroscopically closes this ventilation channel. However, the label has pores of a size that allows air to pass through. In particular, pore sizes of between 0.1 μm and 0.3 μm have proven suitable. As regards the preferred flow resistance, the values already mentioned above apply. The flow resistance of the ventilation channel with such an affixed membrane is preferably such that an air quantity of 0.2 ml/s flows through the ventilation channel at a differential pressure that is less than 700 mbar and/or more than 200 mbar.

This label macroscopically closing the ventilation channel, and having microscopic pores, is preferably applied flat to an outer face of the dispenser, in particular on an outer face of the outer container, such that it closes a channel portion penetrating a wall of the dispenser. It can be secured by adhesive bonding in particular, in particular by using a self-adhesive label which is in particular preferably affixed around the penetrating channel portion. In principle, however, it is also possible to use a label applied thermally or by shrinkage. In the case of an adhesively affixed label, it is advantageous to provide surface areas that do not have an adhesive layer in order to avoid the pores in this area being closed by the adhesive.

In advantageous embodiments, the dispenser is designed as a drop dispenser, in particular as an eye drop dispenser. It is in particular a dispenser, particularly a drop dispenser, for dispensing medicines that contain liquid formulations of molecule groups commonly used in ophthalmology (treatment of increased intraocular pressure, glaucoma treatment, treatment of dry eyes, treatment of allergies and inflammations). These molecule groups are in particular alpha-2-agonists (e.g. brimonidine), prostaglandin analogs (e.g. tafluprost, latanoprost, bimatoprost, travoprost), beta blockers (e.g. timolol), and carbonic anhydrase inhibitors (e.g. dorzolamide), furthermore hyaluronic acid compounds, film formers in general (e.g. methylcellulose compounds) and cyclosporin and also antihistamines (e.g. olopatadine and levocabastine), steroids (e.g. loteprednol and dexamethasone) and also NSAIDs (e.g. ketorolac).

BRIEF DESCRIPTION OF THE DRAWINGS

Further aspects and advantages of the invention will become clear from the claims and from the following description of preferred exemplary embodiments of the invention, which are explained with reference to the figures in which;

DETAILED DESCRIPTION OF THE ILLUSTRATIVE EMBODIMENTS

Figure 1:
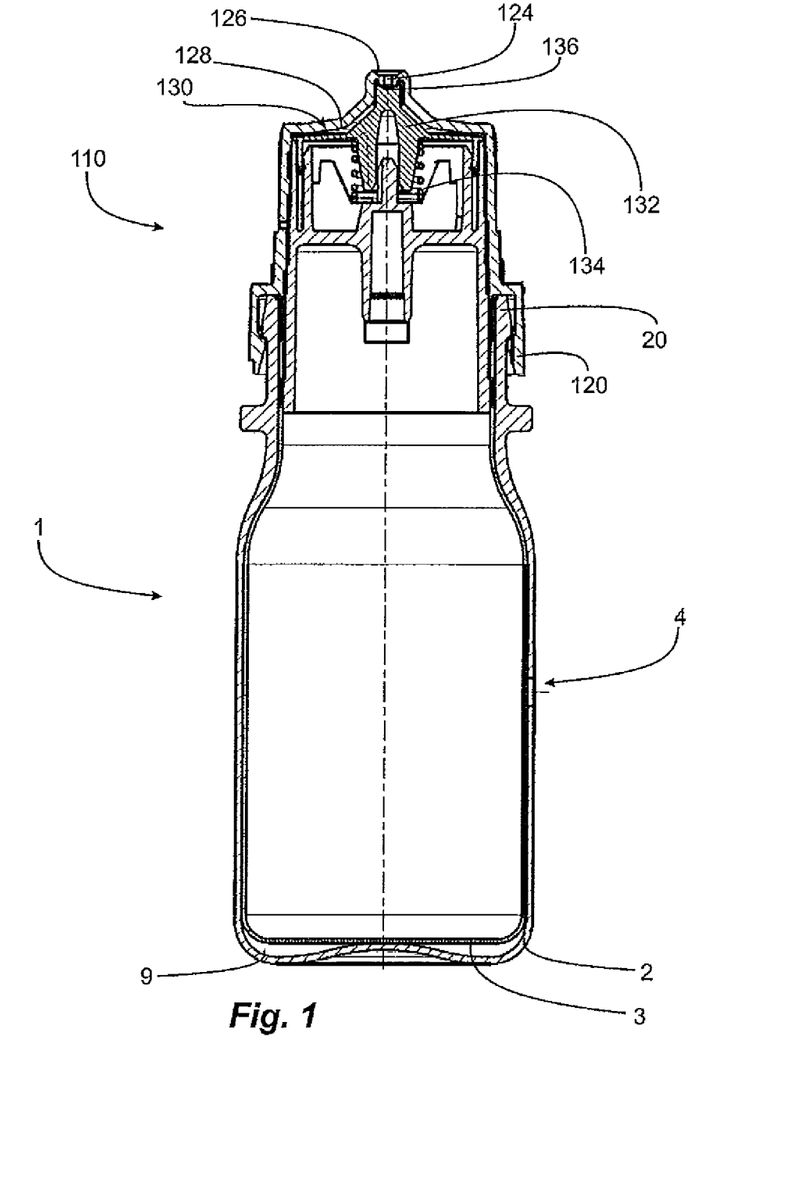
FIG. 1 shows a dispenser which is provided according to the invention with outer container and inner container.
Figure 2A:
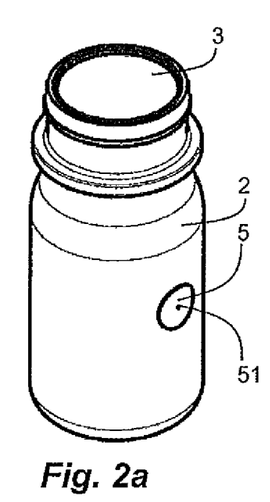
FIGS. 2A to 2D show the outer container and inner container of a first embodiment of a dispenser according to the invention.
Figure 2B:
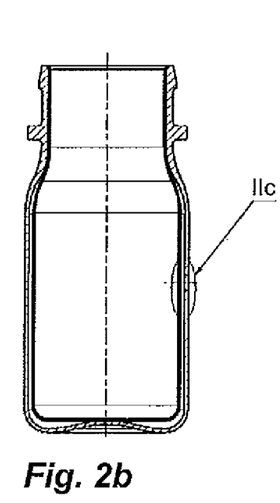
Figure 2C:
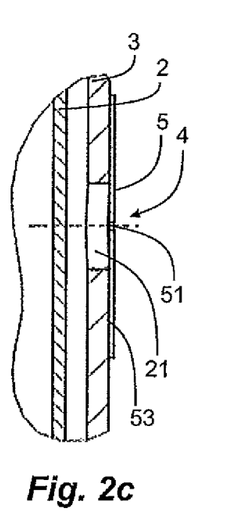
Figure 2D:
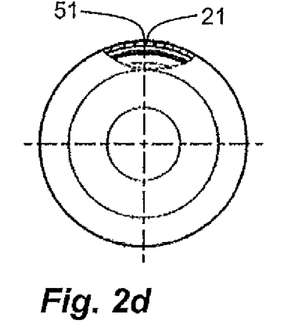

FIG. 1 shows a dispenser according to the invention in a sectional view. The ventilation channel provided here in the dispenser of FIG. 1 is to be understood only as an example. Different configurations of the ventilation channel are set out in detail below.

The dispenser according to the invention as shown in FIG. 1 has a discharge head 110, which is latched onto a container 1 by latching means 20, 120 on both sides. In a manner known per se, the discharge head 110 has an outlet valve 130 with a valve body 132 to which force is applied by a valve spring 134. This valve body 132 closes a discharge opening 124 by means of a valve surface 136.

A drop formation surface 126 is provided on the outside of the discharge opening 124. A valve space 128 is provided between the valve body 132 and an inner face of the housing of the discharge head 110. If, in an upturned position in which the discharge head 110 points downward, the liquid in the container 1 is subjected to pressure by manual compressing of the container 1, this also leads to a pressure increase in the valve space 128. In response to this, the valve body 132 is moved counter to the force of the valve spring 134 and frees a liquid path to the discharge opening 124. This then leads to the liquid being discharged.

The dispenser here is designed as a drop dispenser and is therefore provided with the aforementioned drop formation surface 126. The liquid flowing out through the discharge opening 124 collects on this drop formation surface until it detaches in the form of a drop therefrom.

The embodiment as a drop dispenser is to be understood as one example. Other dispenser types, for example ones that generate a spray jet, can also be configured in the manner according to the invention.

The container 1 is multi-layered. It has an outer container 2 made of an elastic plastic and forming a squeeze bottle. This means that, in order to discharge liquid in the intended manner, the outer container 2 is pressed together, for example with a force of between 5 N and 20 N. When this force ceases, the outer container returns immediately, or after a short interval, to its starting shape shown in FIG. 1. An inner container 3 is arranged inside the outer container 2. This inner container 3 is a dimensionally flexible bag provided to hold the liquid that is to be discharged. This is preferably a pharmaceutical or cosmetic liquid, in the present case in particular a medicament that is to be administered in the form of eye drops. In contrast to the outer container 2, the bag-like inner container 3 is not intended to increase in volume again after completion of a discharge procedure. Instead, provision is made that the volume of the inner container decreases as the dispenser is progressively emptied, without this causing appreciable restoring forces to occur in the walls of the inner container.

Provision is therefore made that a free space 9 between the outer container 2 and the inner container 3 increases in volume as the dispenser is progressively emptied. If this free space were isolated from a surrounding atmosphere, an underpressure would arise that would suppress the discharge of liquid long before the medium in the inner container 3 is used up.

To permit pressure compensation in the free space 9, a ventilation opening/ventilation channel 4 is provided. This connects the free space 9 to a surrounding atmosphere. However, since this pressure compensation would mean that, with the inner container 3 already partially emptied, an overpressure required for the discharge would not be able to build up in the free space upon actuation, the ventilation channel 4 is configured such that it has a sufficiently high flow resistance in order to permit effortless discharge anyway.

The question of how high this flow resistance should be depends on a number of factors, for example the internal volume of the outer container and of the inner container. Particularly in drop dispensers of customary size, which in most cases have an internal volume of approximately 10 ml, it is considered expedient if the flow resistance of the ventilation channel is such that, at an overpressure of 700 mbar in the free space between outer container 2 and inner container 3, not more than 0.2 ml/s flow out through the ventilation channel 4. Moreover, the desired flow resistance also depends on the force with which the outer container 2 is intended to be pressed together and on the medium that is discharged. Further influences are the intended duration of actuation and the anticipated time interval between two discharge procedures.

The views in FIGS. 2A to 7A show various embodiments of the container 1 which are designed to achieve such a flow resistance.

In the embodiment according to FIGS. 2A to 2D, provision is made that the outer container 2 is breached by a comparatively large through-opening 21, which is simple to produce from a manufacturing aspect.

To achieve the increased flow resistance, a label 5 is provided which is preferably designed as a self-adhesive label, i.e. provided with an adhesive layer by means of which it can be secured. This label 5 for its part has a through-opening 51 which has a greatly reduced diameter compared to the through-opening 21. The label 5 is applied to the through-opening 21 such that it closes the latter and leaves only the through-opening 51 free. The desired high flow resistance can be easily achieved in this way.

Figure 3A:
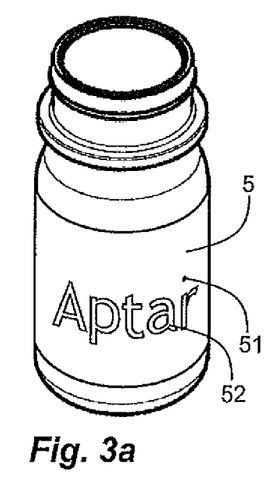
FIG. 3A shows a variant of the container from FIGS. 2A to 2D, FIGS. 4A to 4D show the outer container and inner container of a second embodiment of a dispenser according to the invention.
Figure 4A:
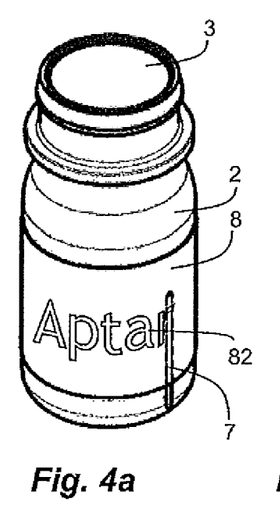
Figures 4B, 4C:
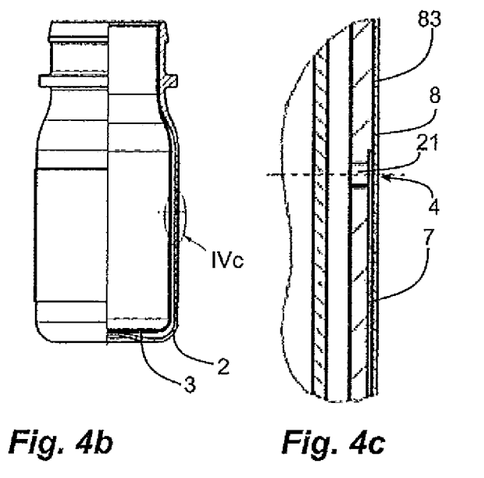
Figure 4D:
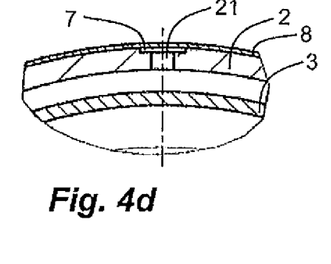

The variant in FIG. 3A differs from the variant in FIGS. 2A to 2D mainly in that a much larger label 5 is provided here which, in a technically identical way to the embodiment in FIGS. 2A to 2D, increases the flow resistance in the ventilation channel 4, since it for this purpose has a through-opening 51 of small cross section. In addition, however, this label 5 is suitably imprinted in order to serve also as an information label which, for example, can show a manufacturer's name 52, directions for use, or details concerning the composition.

The label 5 shown in FIG. 3A can also be designed as a self-adhesive label 5 or as a label 5 that is secured by means of a previously applied layer of adhesive. Another possibility is for the label to be designed as a circumferential shrink-fit label or as a thermally affixed label.

The described labels 5 can be produced directly with said through-opening 51. However, it is also conceivable for the opening to be formed by means of a needle-like body only after the label has been applied. This makes the label 5 easier to position when applying it.

In the embodiment in FIGS. 4A to 4D, provision is made that the outer container 2 is once again breached by a comparatively large through-opening 21. However, in contrast to the embodiment in FIGS. 2A to 2D, this through-opening leads into a depression 7, which extends in the axial direction on the outside of the outer container 2. To ensure that the air flowing out during the actuation of the dispenser can only flow out against a high flow resistance, the groove-like depression 7 is for the most part closed by an adhesive label 8 or shrink-fit label 8. In this embodiment, therefore, in the channel portion provided on the outside of the outer container, the ventilation channel is circumferentially delimited on the one hand by the outer container 2 and on the other hand by the inner face of the label 8. A very simple possibility is thus afforded for creating a long ventilation channel of high flow resistance. In addition, by varying the size of the label, it is also possible to adjust the desired flow resistance in a simple way.

Figure 5A:
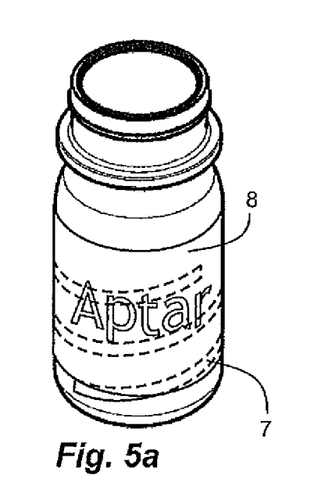
FIG. 5A shows a variant of the container from FIGS. 4A to 4D, FIGS. 6A to 6D show the outer container and inner container of a third embodiment of a dispenser according to the invention.
Figure 6A:
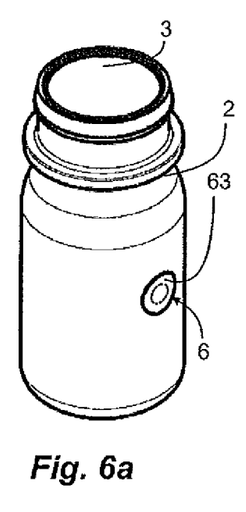
Figure 6B:
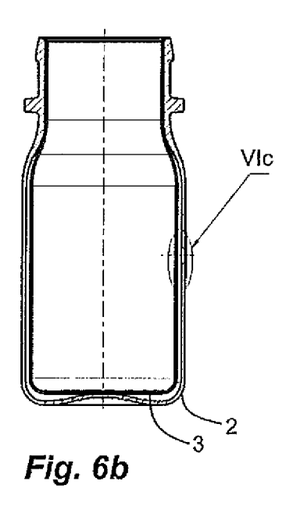
Figure 6C:
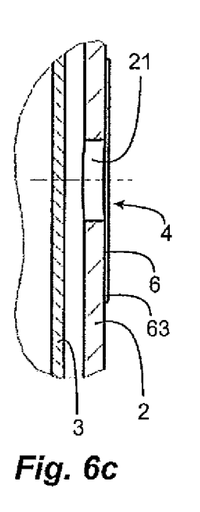
Figure 6D:
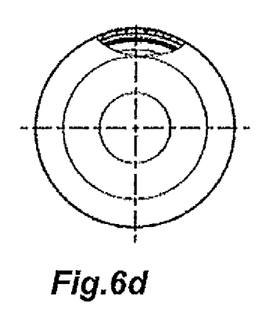

It will be seen from FIG. 5A that, by means of a non-linear extent of the groove-like depression 7, it is possible to achieve a still greater length of the outer portion of the ventilation channel 4. In the variant according to FIG. 5A, it is a helical groove-like depression 7 that is partially closed about the circumference by the label 8.

In the same way as in the embodiment according to FIG. 3A, provision is preferably made that the label 8 not only serves to increase the flow resistance but at the same time is a label of the kind on which information 82 to be read by the user is printed.

The embodiment in FIGS. 6A to 6D corresponds substantially to that of FIGS. 2A to 2D. Here too, provision is made that a through-opening 21 is closed by a comparatively small adhesive label 6. In contrast to the embodiment of FIGS. 2A to 2D, however, the possibility of air exchange is not achieved here through an admittedly small but still macroscopic through-opening, but instead by the label 6 being designed with microscopic pores whose mean diameter is preferably smaller than 0.5 µm. To ensure that these pores are not closed by the inner adhesive layer 63 on the label 6, it is advantageous if the label 6 has no adhesive 63 in a central area but has this only in the edge area.

Figure 7A:
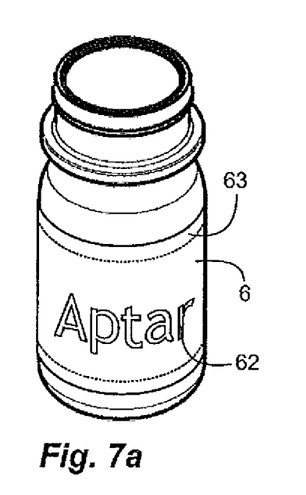
FIG. 7A shows a variant of the container from FIGS. 4A to 4D.

FIG. 7A shows that, in this embodiment too, the label 6 can be used both for increasing the flow resistance and also for applying product information. In the example in FIG. 7A, the preferably circumferential label 6 is provided with a layer of adhesive at edge areas 63. However, it is instead also possible to use a shrink-fit label.

The invention claimed is:

1. A dispenser for discharging a pharmaceutical or cosmetic free-flowing medium, comprising:
    a discharge head having a discharge opening; and
    a container for storing the free-flowing medium prior to discharge, the container comprising an elastically deformable outer container and a dimensionally flexible inner container, the inner container receiving the medium and being arranged in an interior of the outer container;
    wherein a ventilation channel is provided, through which the interior of the outer container is connected to an environment for pressure compensation by compensating air;
    wherein the ventilation channel is delimited in at least some regions by a label;
    wherein the ventilation channel is designed in at least some regions as a capillary channel; and
    wherein the ventilation channel has a flow resistance which is dimensioned such that, when the outer container is pressed together, a pressure sufficient to discharge the medium can be built up in the outer container, wherein the flow resistance is sufficiently high that a volumetric flow rate does not exceed 0.2 ml/sec at a pressure difference of 700 mbar between the outer container and the environment.

2. The dispenser as claimed in claim 1, wherein a channel portion of the ventilation channel is formed jointly by:
    a groove-like elongate depression in a channel component, wherein the channel component is formed by the outer container, and
    the label, which is applied to the channel component, such that the channel portion is closed circumferentially by the depression and the label.

3. The dispenser as claimed in claim 1, wherein the label is printed.

4. The dispenser as claimed in claim 1, wherein the flow resistance is sufficiently low that the volumetric flow rate is not less than 0.2 ml/sec at a pressure difference of 400 mbar between the outer container and the environment.

5. The dispenser as claimed in claim 1, wherein the ventilation channel has a spiral shape or helical shape in at least some regions.

6. The dispenser as claimed in claim 1, wherein the label is self-adhesive in at least some regions.

7. A dispenser for discharging a pharmaceutical or cosmetic free-flowing medium, comprising:
    a discharge head having a discharge opening; and
    a container for storing the free-flowing medium prior to discharge, the container comprising an elastically deformable outer container and a dimensionally flexible inner container, the inner container receiving the medium and being arranged in an interior of the outer container;
    wherein a ventilation channel is provided, through which the interior of the outer container is connected to an environment for pressure compensation by compensating air;
    wherein the ventilation channel is delimited in at least some regions by a label; and
    wherein the ventilation channel is designed in at least some regions as a capillary channel, wherein the capillary channel has a minimal cross-sectional surface area that is smaller than 1 $mm^2$, and wherein a quotient of a length of the capillary channel and of a mean of the cross-sectional surface area of the capillary channel is greater than 150 $mm^{-1}$.

8. The dispenser as claimed in claim 7, wherein the label is self-adhesive in at least some regions.

9. The dispenser as claimed in claim 7, wherein a channel portion of the ventilation channel is formed jointly by:
    a groove-like elongate depression in a channel component, wherein the channel component is formed by the outer container, and
    the label, which is applied to the channel component, such that the channel portion is closed circumferentially by the depression and the label.

10. The dispenser as claimed in claim 7, wherein the label is printed.

11. The dispenser as claimed in claim 7, wherein the ventilation channel has a flow resistance which is dimensioned such that, when the outer container is pressed together, a pressure sufficient to discharge the medium can be built up in the outer container, wherein the ventilation channel for this purpose has a flow resistance which is sufficiently high that a volumetric flow rate does not exceed 0.2 ml/sec at a pressure difference of 700 mbar between the outer container and the environment.

12. The dispenser as claimed in claim 11, wherein the ventilation channel has a flow resistance which is sufficiently low that the volumetric flow rate is not less than 0.2 ml/sec at a pressure difference of 400 mbar between the outer container and the environment.

13. The dispenser as claimed in claim 7, wherein the ventilation channel has a spiral shape or helical shape in at least some regions.

14. A dispenser for discharging a medium, comprising:
a discharge head having a discharge opening; and
a container for storing the medium prior to discharge, the container comprising an elastically deformable outer container and a dimensionally flexible inner container, the inner container for receiving the medium and being arranged in an interior of the outer container;
the container including a ventilation channel through which the interior of the outer container is connected to an environment for pressure compensation by compensating air;
the ventilation channel being delimited in at least some regions by a label; and
at least a portion of the ventilation channel comprising a capillary channel, the ventilation channel always maintaining an open condition during inward deformation of the outer container;
wherein the ventilation channel has a flow resistance which is dimensioned such that, when the outer container is pressed together, a pressure sufficient to discharge the medium can be built up in the outer container, wherein the ventilation channel for this purpose has a flow resistance which is sufficiently high that a volumetric flow rate does not exceed 0.2 ml/sec at a pressure difference of 700 mbar between the outer container and the environment.

15. The dispenser as claimed in claim 14, wherein a channel portion of the ventilation channel is formed jointly by:
a groove-like elongate depression in a channel component, wherein the channel component is formed by the outer container, and
the label, which is applied to the channel component, such that the channel portion is closed circumferentially by the depression and the label.

16. A dispenser for discharging a medium, comprising:
a discharge head having a discharge opening; and
a container for storing the medium prior to discharge, the container comprising an elastically deformable outer container and a dimensionally flexible inner container, the inner container for receiving the medium and being arranged in an interior of the outer container;
the container including a ventilation channel through which the interior of the outer container is connected to an environment for pressure compensation by compensating air;
the ventilation channel being delimited in at least some regions by a label; and
at least a portion of the ventilation channel comprising a capillary channel, the ventilation channel always maintaining an open condition during inward deformation of the outer container;
wherein the ventilation channel has a flow resistance which is sufficiently low that the volumetric flow rate is not less than 0.2 ml/sec at a pressure difference of 400 mbar between the outer container and the environment.

* * * * *